(12) United States Patent
Patvibul et al.

(10) Patent No.: US 9,931,450 B2
(45) Date of Patent: Apr. 3, 2018

(54) BREAST PUMP ADAPTOR AND METHOD OF FILLING BAG

(71) Applicant: Inteplast Group, Ltd., Livingston, NJ (US)

(72) Inventors: Chatporn Patvibul, Chonburi (TH); Sema Srisai, Chonburi (TH); Decha Boontawee, Chonburi (TH); Santi Phalphai, Chonburi (TH)

(73) Assignee: Inteplast Group Corporation, Livingston, NJ (US)

( * ) Notice: Subject to any disclaimer, the term of this patent is extended or adjusted under 35 U.S.C. 154(b) by 99 days.

(21) Appl. No.: 14/925,222

(22) Filed: Oct. 28, 2015

(65) Prior Publication Data

US 2016/0114090 A1    Apr. 28, 2016

Related U.S. Application Data

(60) Provisional application No. 62/069,733, filed on Oct. 28, 2014.

(51) Int. Cl.
    *A61M 1/06*    (2006.01)
(52) U.S. Cl.
    CPC .................. *A61M 1/062* (2014.02)
(58) Field of Classification Search
    CPC A61M 1/06; A61M 1/062; A61J 9/001; A61J 9/006; B65D 33/004
    See application file for complete search history.

(56) References Cited

U.S. PATENT DOCUMENTS

| | | | |
|---|---|---|---|
| 4,850,496 A | 7/1989 | Rudell et al. | |
| 5,261,553 A * | 11/1993 | Mueller | B65F 1/06 220/495.1 |
| D486,224 S | 2/2004 | Gay, III | |
| D486,225 S | 2/2004 | Gay, III | |
| 6,962,439 B2 | 11/2005 | Taheri | |
| 6,991,121 B1 | 1/2006 | Kipperman et al. | |
| D633,797 S | 3/2011 | Cresswell et al. | |
| 8,357,116 B2 | 1/2013 | Simdon | |
| D763,435 S | 8/2016 | Patvibul et al. | |

(Continued)

OTHER PUBLICATIONS

Merriam-Webster.com, Definition of "envelope", https://www.merriam-webster.com/dictionary/envelope.*

(Continued)

*Primary Examiner* — Laura Bouchelle
*Assistant Examiner* — Tasnim M Ahmed
(74) *Attorney, Agent, or Firm* — Senniger Powers LLP

(57) ABSTRACT

An adaptor, system, and method for collecting for a breast pump. A breast milk bag has a hole adjacent an end margin. The bag can have a reclosable seal and a zone of weakness for separating a sealed portion from a header. An adaptor has inlet end and an outlet end and defines a flow passage. The inlet end is securable to the outlet of the breast pump so liquid therefrom can flow through the flow passage. A slot extends through the adaptor wall to at least partially define a retainer for extending through the hole to mount the bag on the adapter. In a method of use, the bag is secured to the adaptor using the retainer, filled with breast milk, sealed while secured to the adaptor, and the sealed portion of the bag can be removed by tearing the bag along the zone of weakness.

16 Claims, 8 Drawing Sheets

(56) References Cited

U.S. PATENT DOCUMENTS

| | | |
|---|---|---|
| 2002/0156419 A1 | 10/2002 | Silver et al. |
| 2006/0074379 A1* | 4/2006 | Hunt .................. A61J 9/005 |
| | | 604/74 |
| 2007/0173756 A1 | 7/2007 | Krebs et al. |
| 2008/0041859 A1 | 2/2008 | Teglbjarg |
| 2010/0262072 A1 | 10/2010 | Attolini et al. |
| 2011/0098639 A1 | 4/2011 | Kirchner |
| 2012/0022445 A1 | 1/2012 | Jones |
| 2012/0041365 A1 | 2/2012 | Simdon |
| 2012/0051670 A1 | 3/2012 | Matias |
| 2014/0102918 A1 | 4/2014 | Eitrheim et al. |
| 2014/0107608 A1 | 4/2014 | McBean et al. |
| 2014/0213964 A1* | 7/2014 | Taheri .................. A61M 1/06 |
| | | 604/74 |
| 2014/0343486 A1 | 11/2014 | Taheri |
| 2015/0024085 A1 | 1/2015 | McBean et al. |
| 2015/0144584 A1 | 5/2015 | Renz et al. |
| 2016/0015603 A1 | 1/2016 | McBean et al. |
| 2016/0114090 A1 | 4/2016 | Patvibul et al. |
| 2016/0287766 A1 | 10/2016 | Bambino et al. |
| 2016/0317728 A1 | 11/2016 | Lewis et al. |
| 2017/0021068 A1 | 1/2017 | Gaskin et al. |

OTHER PUBLICATIONS

Medela, Inc., Pump & Save product sheet, 2 pages, (C) 2012, Medela, Inc.

* cited by examiner

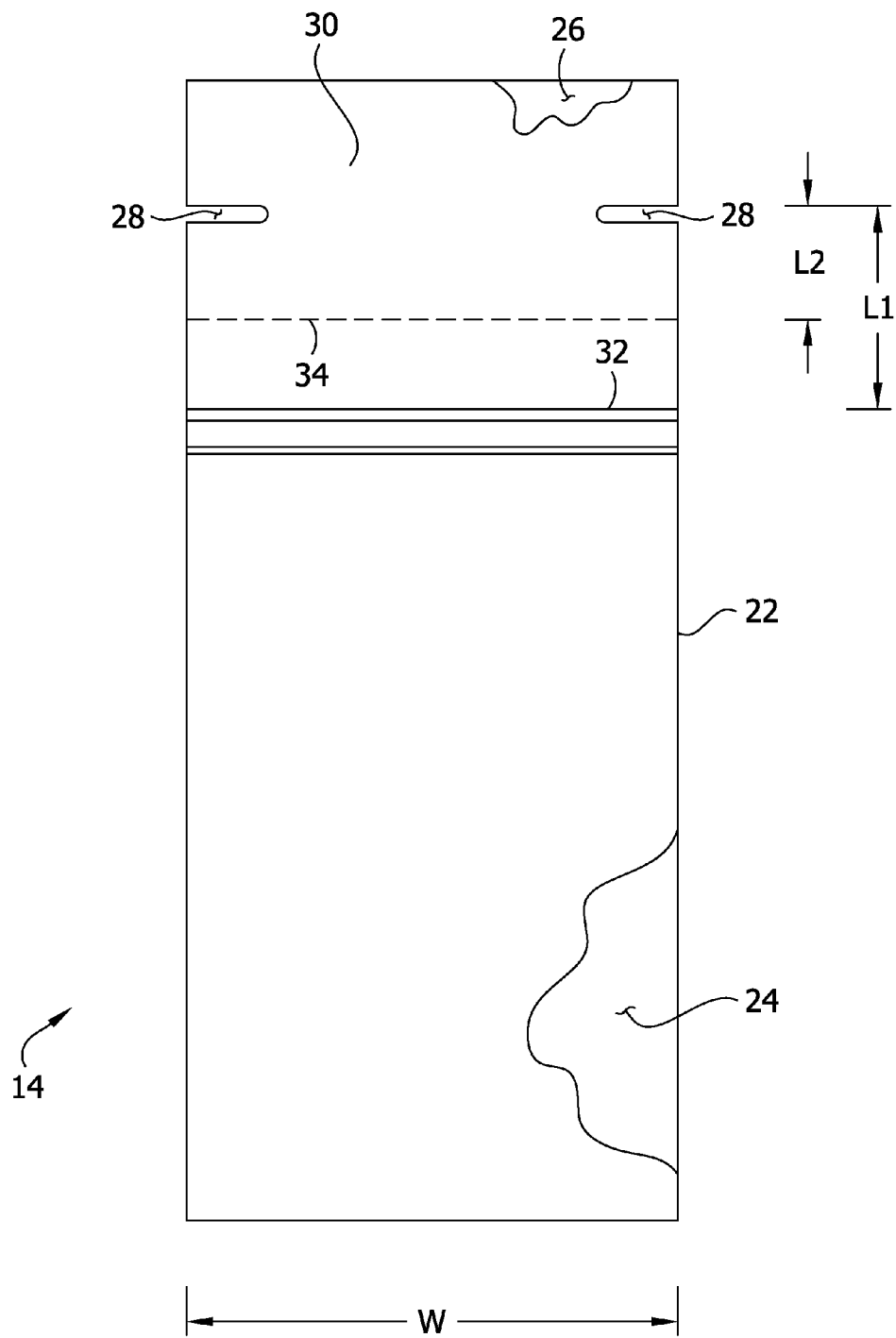

BREAST PUMP ADAPTOR AND METHOD OF FILLING BAG

CROSS REFERENCE TO RELATED APPLICATIONS

The present application claims priority to U.S. Provisional Patent Application Ser. No. 62/069,733, entitled BREAST PUMP ADAPTOR AND METHOD OF FILLING BAG, which is hereby incorporated by reference into the present disclosure.

FIELD OF THE DISCLOSURE

Aspects of the present disclosure relate generally to systems for filling a bag with liquid dispensed from the outlet of a breast pump. More specifically, aspects of the present disclosure relate to an adaptor for securing a bag to a breast pump.

BACKGROUND OF THE DISCLOSURE

Breast pumps are configured to pump breast milk into a receptacle. Conventional breast pumps attach to a plastic feeding bottle. The pumped milk is deposited directly into the feeding bottle. Certain breast pump systems are configured to pump directly into a flexible storage bag. Many of these systems require the bag to be contained in a rigid vessel during pumping. In some of the systems, the bag hangs directly from the pump or an adaptor connected thereto. One adaptor for securing a bag to a breast pump includes a cylindrical conduit with diametrically opposed mounting hooks extending radially outward from the conduit. Each of the mounting hooks includes a radially outwardly projecting portion and an upwardly extending portion. To secure a bag to the adaptor, holes in the bag are threaded over the upwardly extending portion of the mounting hooks and onto the radially outwardly projecting portion of the mounting hooks. The bag hangs down from the radially outwardly projecting portion of the mounting hooks during use. Since the mounting hooks in this design project radially outwardly from the conduit, the bag opening must be larger than the conduit so that the holes in the bag can be threaded onto the hooks. As a result, the bag does not closely conform to the conduit, which can permit air and contaminants to enter the bag. In addition, because the mounting hooks extend in two directions (i.e., radially outward and upward) removing the bag from the adaptor when it is filled with liquid can be difficult. Moreover, the positioning of the adaptor with the bag makes it impossible to seal the bag prior to removal of the bag from the adaptor.

SUMMARY

In one aspect, an adaptor secures a bag comprising a bag body defining a bag interior and a bag opening to a breast pump to receive liquid dispensed from an outlet of the breast pump in the bag interior. The bag body comprises at least one hole at an end margin thereof adjacent the bag opening. The adaptor comprises a liquid flow passage, an inlet end portion, and an outlet end portion and a wall extending circumferentially about the liquid flow passage and longitudinally between the inlet end portion and the outlet end portion of the adaptor. The inlet end portion of the adaptor is configured to attach to the outlet of the breast pump so that liquid dispensed from the outlet of the breast pump passes through the liquid flow passage and is dispensed from the outlet end portion of the adaptor. The adaptor further comprises at least one slot extending through the wall and a retainer at least partially defined by the slot. The retainer is configured to extend through the at least one hole in the bag body to secure the bag to the breast pump to receive the liquid dispensed from the outlet end portion of the adaptor.

In another aspect, a method of filling a bag with breast milk. The bag comprises a bag body defining a bag interior, a bag opening adjacent a top edge of the bag, and a reclosable seal extending across a width of the bag. The method comprises securing the bag to a breast pump with an adaptor so that liquid dispensed from an outlet of the breast pump is deposited into the bag interior. Liquid is pumped into the secured bag using the breast pump until the bag interior is at least partially filled with liquid. The partially filled bag is sealed using the reclosable seal while the bag is secured to the breast pump with the adaptor. At least a portion of the bag body that is at least partially filled with liquid and sealed with the reclosable seal is removed from the breast pump and adaptor.

In yet another aspect, a system for collecting breast milk comprises at least one bag comprising a bag body defining a bag interior and a bag opening. The bag body comprises at least one hole at an end margin thereof adjacent the bag opening. A reclosable seal configured to selectively seal the bag is spaced apart from the at least one hole relative to the end margin, and a zone of weakness is spaced apart between the end margin and the reclosable seal and defines a header portion of the bag. An adaptor for securing the bag to a breast pump comprises a wall having an inlet end portion and a spaced apart outlet end portion. The wall defines a flow passage extending along the axis through the inlet end portion and outlet end portion. The inlet end portion is configured to attach to an outlet of a breast pump so that liquid dispensed from the outlet of the breast pump passes through the liquid flow passage and is dispensed from the outlet end portion of the adaptor. The adaptor further comprises a retainer configured to extend through the at least one hole in the bag body to secure the bag to the breast pump to receive the liquid dispensed from the outlet end portion of the adaptor. The adaptor and the bag are sized and arranged so that, when the retainer secures the bag to the adaptor, the reclosable seal can be selectively sealed and the bag body can be subsequently torn along the zone of weakness to separate a sealed portion of the bag from the header portion without removing the header portion from the adaptor.

Other objects and features will be in part apparent and in part pointed out hereinafter.

BRIEF DESCRIPTION OF THE DRAWINGS

FIG. 3 is a fragmentary elevation of a bag of the breast pump system;

Corresponding reference characters indicate corresponding parts throughout the drawings.

DETAILED DESCRIPTION

Figure 1:
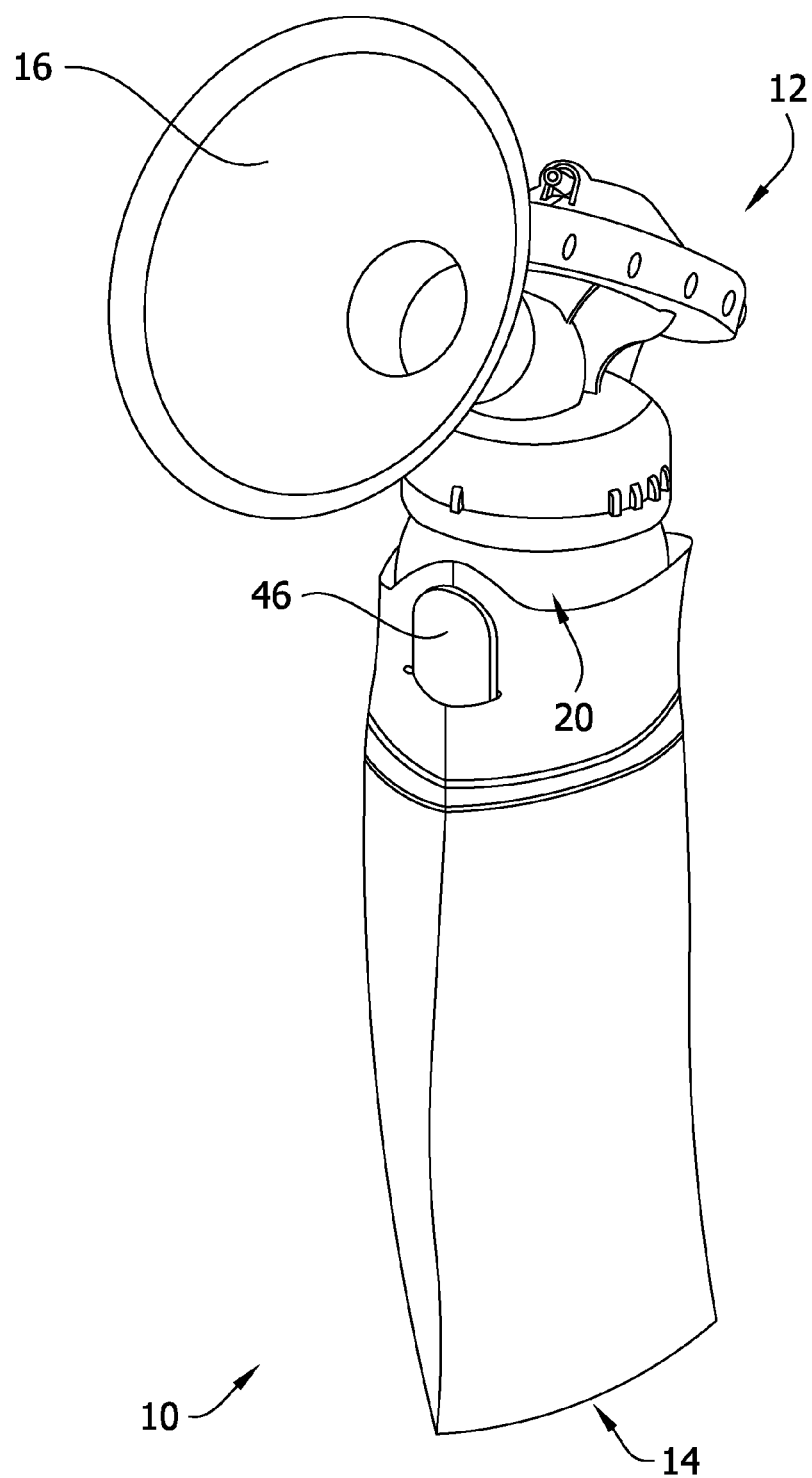
FIG. 1 is a perspective of a breast pump system.
Figure 2:
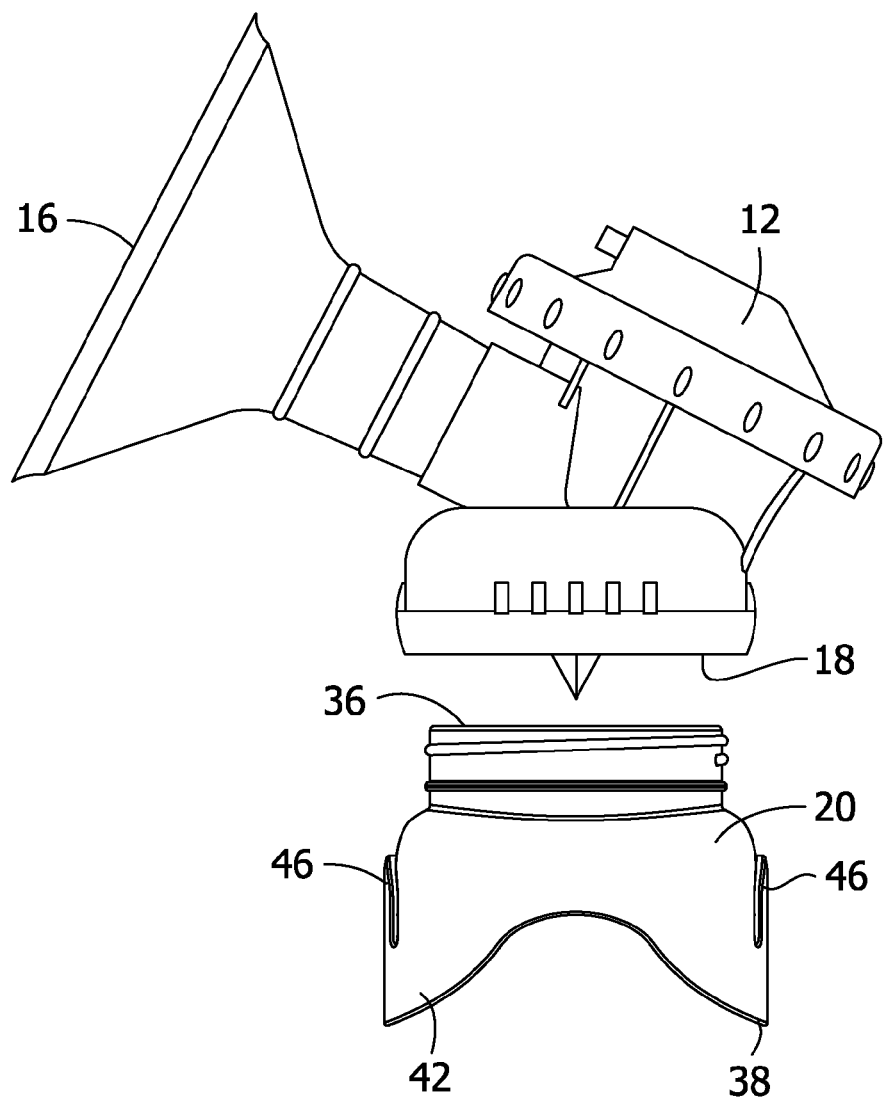
FIG. 2 is an elevation of a breast pump and an adaptor from the breast pump system in which the adaptor is detached from the breast pump.

Referring to FIGS. 1 and 2, a breast pump system is generally indicated at reference number 10. The breast pump system 10 includes a breast pump 12, a bag 14, and an adaptor 20 for attaching the bag to the pump so that breast milk can be delivered into the bag. The breast pump 12 has a fluid inlet portion 16 and a fluid outlet portion 18. The inlet portion 16 of the breast pump 12 is configured to engage the breast of a user and pump breast milk (broadly liquid) into a receptacle, such as a bottle (not shown), the bag 14, or other suitable container. The outlet portion 18 of the breast pump 12 is configured to threadably mate with the threaded end of a rigid plastic bottle (e.g., a baby bottle). The breast pump 12 pumps liquid from the inlet portion 16 through the pump and dispenses the liquid out the outlet portion 18. The adaptor 20 attaches to the outlet portion 18 of the breast pump 12 for attaching the flexible bag 14 to allow milk to be pumped into the bag.

Figure 3A:
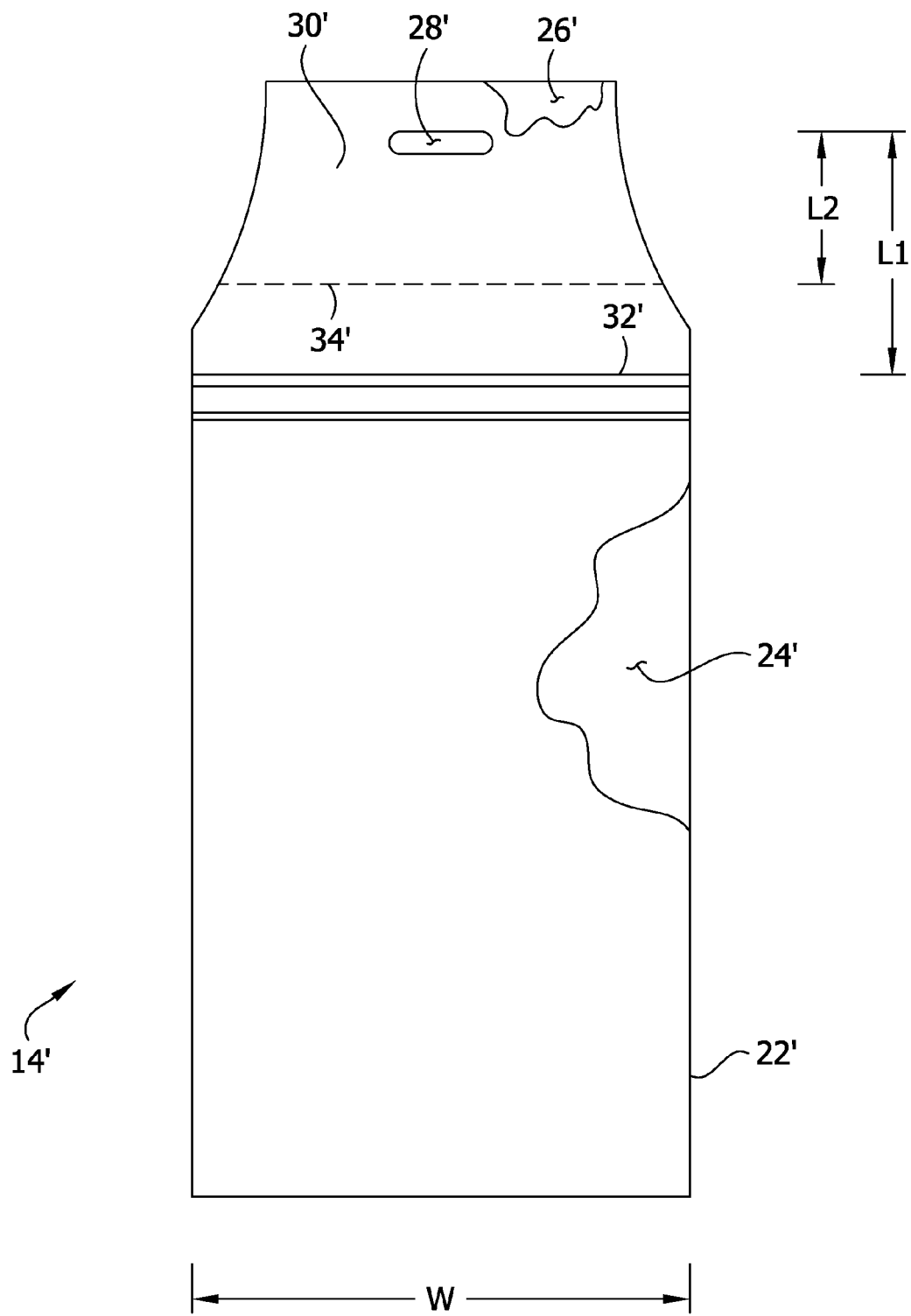
FIG. 3A is a fragmentary elevation of another bag.

Referring to FIG. 3, the bag 14 comprises a bag body 22 defining a bag interior 24 and a bag opening 26. The bag 14 also includes a pair of holes 28 in the bag body 22 for hanging the bag from the adaptor 20. The holes 28 are located at an end margin 30 of the bag body 22 adjacent the bag opening 26. In a preferred embodiment, the holes 28 are positioned at side edges of the bag (FIG. 3) (e.g., at the joints between front and rear panels of the bag). However, referring to FIG. 3A, in another embodiment of a bag 14', holes 28' are positioned away from the side edges of the bag (e.g., positioned at a location along the width W of the bag body 22' on one or both of the front and rear panels of the bag). Features of the bag 14' that correspond with features of the bag 14 are given the same reference number, with an apostrophe. Referring again to FIG. 3, a reclosable seal 32 extends across a width W of the bag 14 and is spaced apart from the holes 28, away from the end margin 30 of the bag. The reclosable seal 32 of the illustrated bag 14 is spaced apart from the holes 28 a first length L1. Though the illustrated bag 14 uses a reclosable seal, it is contemplated that other types of bags can use other types of seals or that a seal may be omitted without departing from the scope of the invention. As shown in FIG. 3A, the bag 14', like the bag 14, has a bag opening 26' at the top end margin 30' and a reclosable seal 32' configured to selectively seal the bag opening.

Referring again to FIG. 3, in a preferred embodiment, perforations 34, which create a zone of weakness in the bag body 22, extend across the width W of the bag body and define a tear path in the bag 14 (the bag 14' of FIG. 3A likewise includes perforations 34' defining a zone of weakness). Preferably, the perforations 34 are positioned between the holes 28 in the end margin 30 of the bag and the reclosable seal 32. The perforations 34 are spaced apart from the holes 28 a second length L2. Perforations can also extend across the width of the bag at the same level as the holes 28 (not shown), provided they are constructed and arranged to prevent the bag body from tearing under normal use, when the bag 14 is suspended from the adaptor 20 and the bag interior 26 is filled with liquid. The zone of weakness bounds an inboard end of a header portion of the bag. The bag 14 can also include any of the following features: tamper resistance, easy opening seals, grip strips, dedicated labeling spaces, etc. Other suitable features of a bag for use with the breast pump system 10 are described in U.S. Pat. No. 6,962,439, which is hereby incorporated by reference in its entirety.

Figure 4:
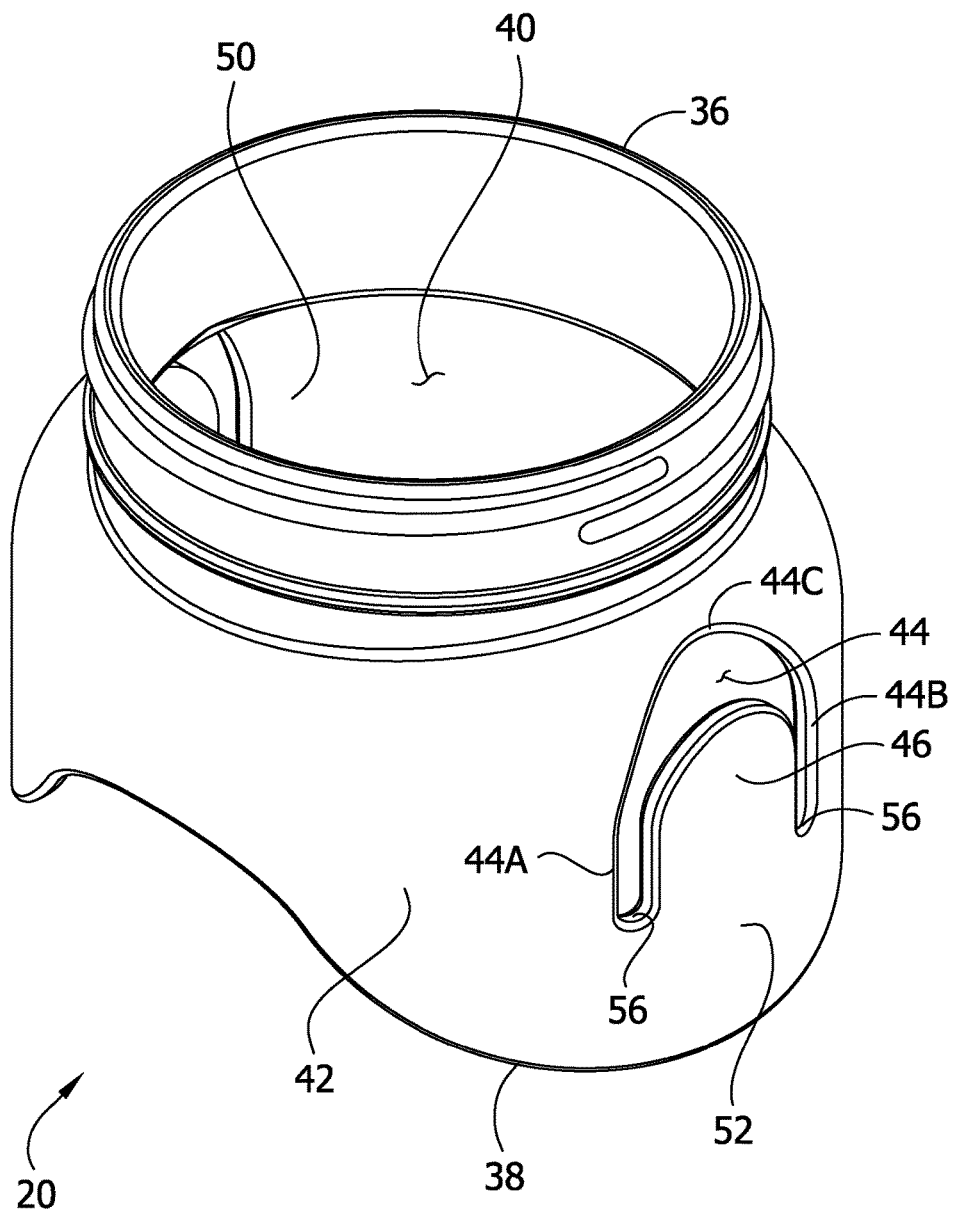
FIG. 4 is a perspective of the adaptor.
Figure 5:
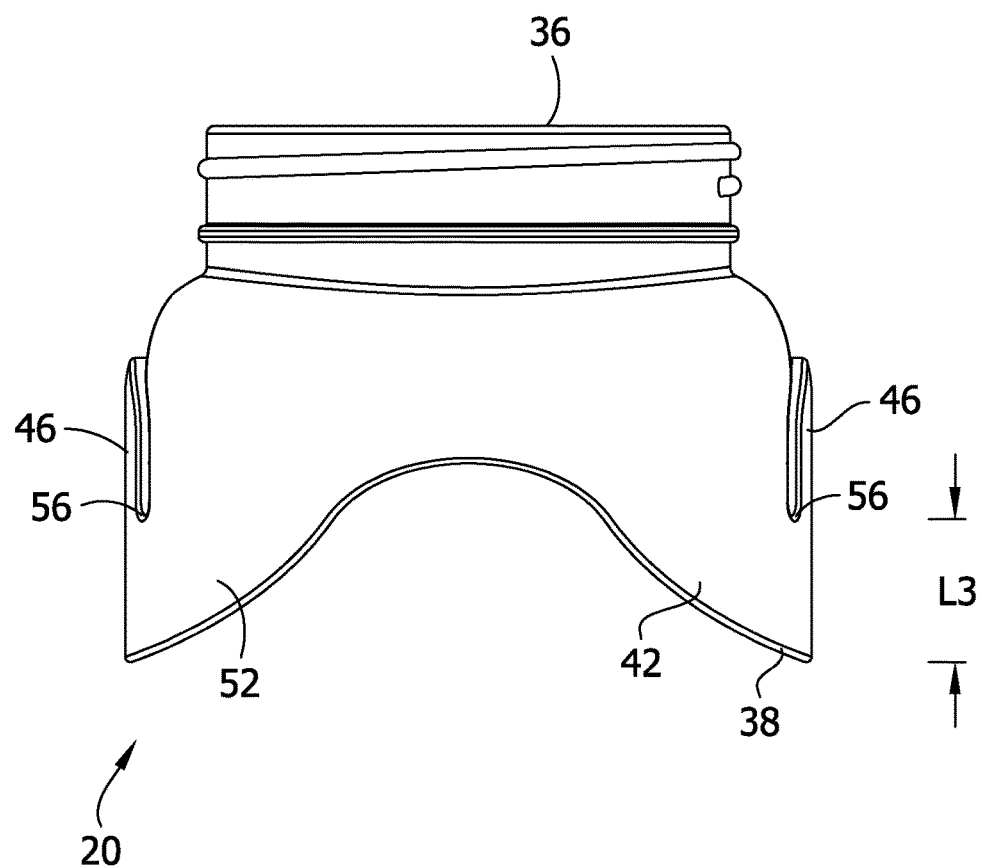
FIG. 5 is a front elevation of the adaptor.
Figure 6:
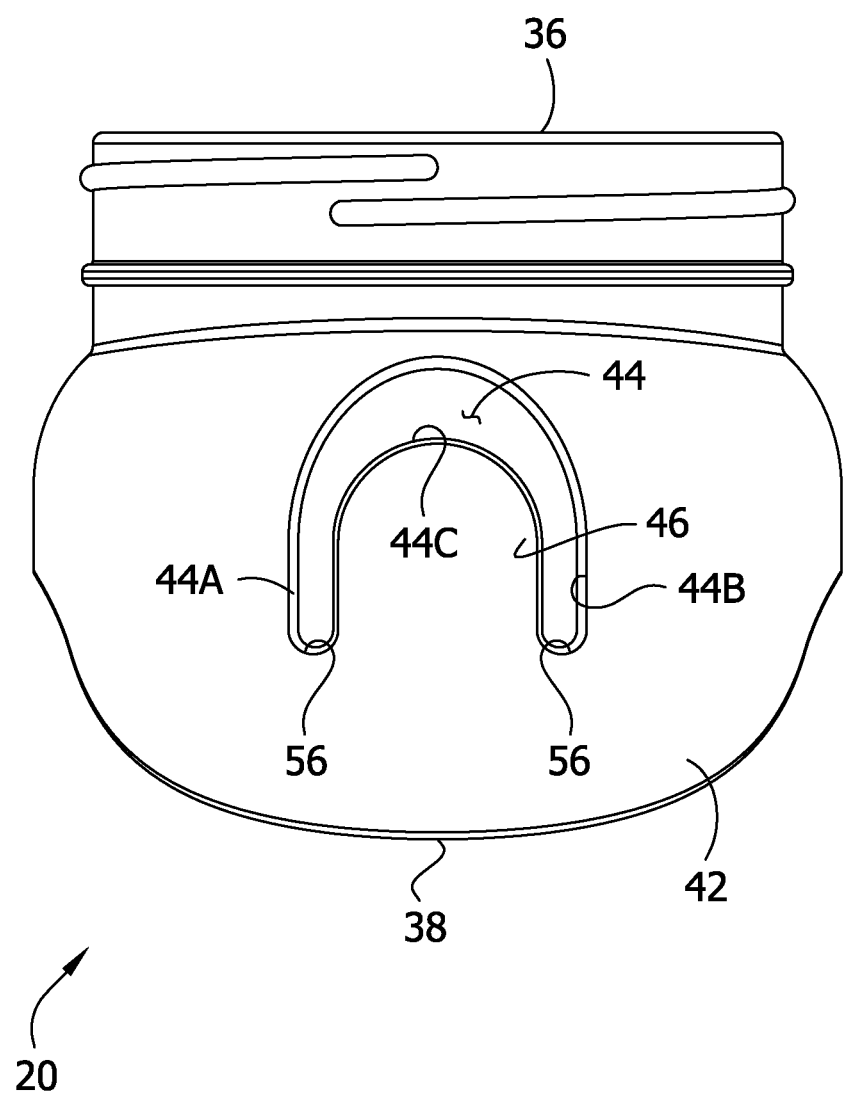
FIG. 6 is a side elevation of the adaptor.
Figure 7:
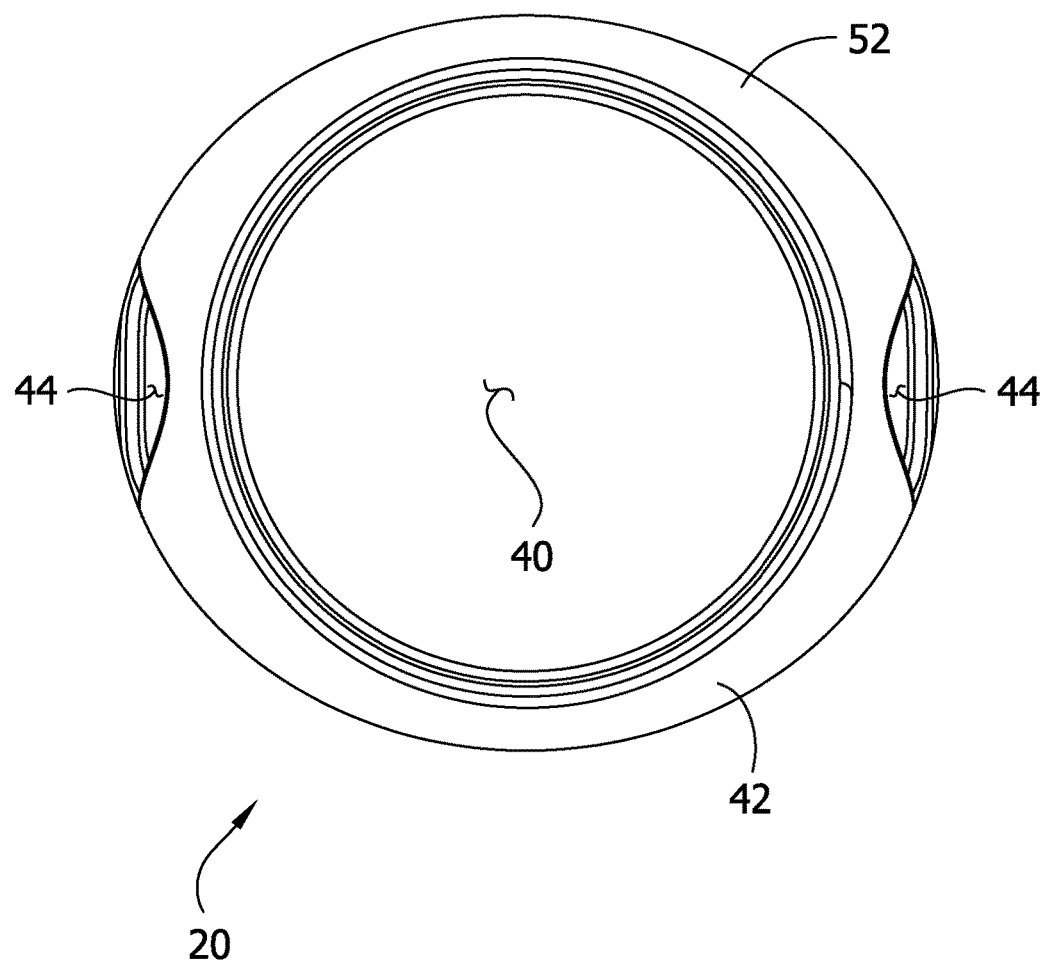
FIG. 7 is a top plan of the adaptor.

Referring to FIGS. 1-2 and 4-7, the adaptor 20 is configured to secure the bag 14 to the breast pump 12 to receive liquid dispensed through the outlet portion 18 of the breast pump in the bag interior 24. The adaptor 20 has an inlet end portion 36 and an outlet end portion 38 that is spaced apart from the inlet end portion. A liquid flow passage 40 extends from the inlet end portion 36 to the outlet end portion 38. The adaptor 20 includes a wall 42 that extends circumferentially around the liquid flow passage 40 and longitudinally between the inlet end portion 36 and the outlet end portion 38. Referring particularly to FIGS. 4-6, the lower edge of the wall 42 is shaped so that the wall extends down further on two of the opposing sides than on the other two opposing sides. The two opposing sides at which the wall 42 extends down a lesser distance provide more space for the user to close the bag 14 while the bag is secured to the adaptor 20. The inlet end portion 36 of the adaptor 20 is configured to be attached to the outlet portion 18 of the pump 12. In the illustrated embodiment, the inlet end portion 36 of the adaptor 20 is configured to threadably mate with the outlet portion 18 of the breast pump 12. For example, the inlet end portion 36 may be formed like the top of a baby bottle. When the adaptor 20 is attached to the breast pump 12 (i.e., when the inlet end portion 36 of the adaptor is threaded into the outlet portion 18 of the breast pump), liquid dispensed from the outlet portion of the breast pump is received in the liquid flow passage 40. The liquid passes through the flow passage 40 and is dispensed from the outlet end 38 of the adaptor 20. The bag 14 is secured to the adaptor 20 so that the liquid dispensed from the outlet end 38 of the adaptor 20 is received in the bag interior 24.

Referring to FIGS. 1-7, the adaptor 20 includes two slots 44 that extend through the wall 42 on opposite sides of the adaptor. Each slot 44 defines a boundary of a retainer tab 46 (broadly, "a retainer"). Each of the retainer tabs 46 is configured to extend through one of the holes 28 in the bag 14 to retain the bag and thereby secure the bag to the breast pump 12. Each of the slots 44 has a substantially inverted U-shape and defines the boundary around three sides of one of the retainer tabs 46. Each slot 44 has a pair of leg portions 44A, 44B and a top connecting portion 44C. Bag support surfaces 56 are located at the bottoms of the leg portions 44A, 44B. In the illustrated embodiment, the leg portions 44A, 44B of each slot 44 are generally straight and oriented substantially parallel to one another. However, in other embodiments, it is contemplated that the leg portions 44A, 44B can be non-straight or oriented at an angle to one another. The connecting portion 44C of each slot 44 is generally arcuate and is wider than the leg portions 44A, 44B.

The retainer tabs 46 are integrally formed with the wall 42 of the adaptor 20 and do not project outwardly away from the wall. In the illustrated embodiment, the retainer tabs 46 lie within an envelope defined by the shape of the outboard surface 52 of the wall 42. The wall 42 tapers toward the inlet end portion 36 so that the connecting portion 44C of the slot 44 has a lateral expanse (see FIG. 7). The lateral expanse provides the space needed to place the bag 14 on the adaptor 20 with the retainers 46 received through the holes 28 without having to open the bag widely or cant the bag to connect it to the adaptor. The wall 42 of the adaptor 20 has an inboard surface 50 and an outboard surface 52. When the bag 14 is retained by the retainer tabs 46, the inboard surface 50 of the wall 42 at each retainer tab engages a portion of the end margin 30 of the bag body 22. Likewise, the outboard surface 52 of the wall 42 adjacent each retainer tab 46 engages another portion of the bag body 22. Adjacent each of the two holes 28, the end margin 30 of the bag body 22 is received in one of the slots 44 between the inboard surface 50 of the wall 42 at the retainer tab 46 and the outboard surface 52 of the wall adjacent the retainer tab like a sheet of paper received in a paper clip. When the bag 14 is retained by the retainer tabs 46, the end margin 30 of the bag 14 is supported adjacent the holes 28 by the bag support surfaces 56 of the adaptor 20. The bag support surfaces 56 support the bag 14 as it hangs down away from the adaptor.

Because the retainer tab 46 is integrally formed with the wall 42 and does not project radially outwardly from the wall, threading each retainer tab 46 though one of the holes 28 in the bag body 22 simply requires the bag to be pulled downward with the hole in proper alignment relative the retainer tab. Preferably, when the retainer tabs 46 extend through the holes 28 in the bag body 22 to secure the bag 14 to the breast pump 12, the bag opening 26 extends around the adaptor wall 42. Because the retainer tab 46 is integrally formed with the wall 42 and does not project radially outwardly from the wall, the adaptor 20 can be used with a bag 14 whose bag opening 26 substantially conforms to the shape of the adaptor wall. For example, the length of the perimeter of the bag opening 26 can be between about 101% and about 130% of the length of the perimeter of the adaptor wall 42. The close conformance of the bag opening 26 to the adaptor wall 42 securely retains the bag 14 in place with respect to the adaptor 20 to minimize movement of the bag in use. Likewise, using a bag 14 whose opening 26 substantially conforms to the shape of the outboard surface 52 of the adaptor wall 42 minimizes airflow into the bag interior 24 and therefore minimizes the airborne contaminants that enter the bag. Preferably, when the bag body 22 is supported on the bag support surfaces 56 of the adaptor 20 and retained by the retainer tabs 46, the end margin 30 of the bag body extends up past the top end of the slots 44 (i.e., second length 44B) so as to substantially cover the slots and further prevent contamination. In one example, the top edge of the hole 28 is spaced from the top edge of the bag body 22 by about 20 mm or 0.79 inches or more or at least the distance between the bag support surfaces 56 and the top of connecting portions 44C. In this way, the top margin of the bag body 22 effectively closes the slots 44 in use.

Referring to FIGS. 1, 3, and 5, the adaptor 20 and bag 14 are sized so that the bag can be filled, sealed, and torn along the perforations 34 to release connection of the bag from the adaptor without removing the retainer tabs 46 from the holes 28 in the bag. As discussed above, the reclosable seal 32 of the illustrated bag 14 is spaced apart from the holes 28 a first length L1, and the perforations 34 are spaced apart from the holes 28 a second distance L2. Referring to FIG. 5, the bottom of the outlet end portion 38 of the adaptor 20 is spaced apart from the bag support surfaces 56 a third length L3. Preferably the first length L1 is greater than the third length L3. When the retainer tabs 46 of the adaptor 20 extend through the holes 28 in the bag body 22 and the bag 14 is supported by the bag support surfaces 56, the reclosable seal 32 is spaced beneath the bottom of the outlet end portion 38 of the adaptor 20. Thus the reclosable seal 32 can be used to seal the bag 14 while the bag is supported by the adaptor 20. Likewise, the second length L2 is preferably greater than the third length L3. When the retainer tabs 46 of the adaptor 20 extend through the holes 28 in the bag body 22 and the bag 14 is supported by the bag support surfaces 56, the perforations 34 are spaced apart beneath the bottom of the outlet end portion 38 of the adaptor 20. Thus, after being filled with liquid, the bag 14 can be torn along the perforations 34 to remove the bag and its contents from the adaptor. The header portion of the bag 14 remains secured to the adapter 20 after the filled and sealed portion is removed.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products without departing from the scope of the invention, it is intended that all matter contained in the above description and shown in the accompanying drawings shall be interpreted as illustrative and not in a limiting sense.

What is claimed is:

1. An adaptor for securing a bag comprising a bag body defining a bag interior and a bag opening to a breast pump to receive liquid dispensed from an outlet of the breast pump in the bag interior, the bag body comprising at least one hole at an end margin thereof adjacent the bag opening, the adaptor comprising a liquid flow passage, an inlet end portion, and an outlet end portion and a wall extending circumferentially about the liquid flow passage and longitudinally between the inlet end portion and the outlet end portion of the adaptor, the inlet end portion of the adaptor being configured to attach to the outlet of the breast pump so that liquid dispensed from the outlet of the breast pump passes through the liquid flow passage and is dispensed from the outlet end portion of the adaptor, the adaptor further comprising at least one slot extending through the wall and a retainer at least partially defined by the slot, the retainer being configured to extend through the at least one hole in the bag body to secure the bag to the breast pump to receive the liquid dispensed from the outlet end portion of the adaptor;

wherein the slot comprises a pair of leg portions and a top connecting portion and the wall tapers toward the inlet end portion of the adaptor so that the top connecting portion of the slot extends laterally inward of at least a portion of the retainer.

2. The adaptor in claim 1 further comprising two slots extending through the wall of the adaptor and two retainers, each of the two retainers being at least partially defined by a respective one of the two slots.

3. The adaptor in claim 2 wherein each of the two retainers is configured to extend through a separate hole at the end margin of the bag body to secure the bag to the breast pump to receive the liquid dispensed from the outlet end portion of the adaptor.

4. The adaptor in claim 1 wherein the slot defines a boundary around three sides of the retainer.

5. The adaptor in claim 1 wherein the slot is substantially U-shaped.

6. The adaptor in claim 1 wherein the leg portions of the slot are oriented substantially parallel to one another.

7. The adaptor in claim 6 wherein the connecting portion of the slot is arcuate.

8. The adaptor in claim 1 wherein the wall comprises an inboard surface and an outboard surface and wherein, when the retainer extends through the at least one hole in the bag body, the inboard surface of the wall at the retainer is configured to engage a portion of the end margin of the bag body and the outboard surface of the wall adjacent the retainer is configured to engage another portion of the bag body.

9. The adaptor in claim 1 wherein the retainer is formed as one piece of material with the wall of the adaptor.

10. The adaptor in claim 1 wherein the wall has a height and no portion of the retainer projects radially outward beyond adjacent portions of the wall that are aligned with retainer along the height.

11. The adaptor in claim 1 in combination with the bag, wherein the bag body defines a bag interior and a bag opening adjacent a top edge of the bag, the bag body comprising the at least one hole configured to be received over the retainer to hang the bag from the adaptor to receive liquid dispensed from the breast pump in the bag interior.

12. The combination of the adaptor and the bag as set forth in claim 11 wherein the bag comprises a reclosable seal extending across a width of the bag and being positioned on the bag body with respect to the hole so that the bag is sealable using the reclosable seal while the bag hangs from the adaptor.

13. The combination of the adaptor and the bag as set forth in claim 12 wherein the reclosable seal is positioned on the bag body with respect to the hole so that the bag is sealable using the reclosable seal while the bag hangs from the adaptor and the bag interior is at least partially filled with liquid.

14. The combination of the adaptor and the bag as set forth in claim 13 wherein the bag body further comprises a zone of weakness extending across the width of the bag between the top edge of the bag and the reclosable seal, the bag body being tearable along the zone of weakness to separate a portion of the bag body that is at least partially filled with liquid and sealed with the reclosable seal from a top end margin of the bag body without removing the retainer from the hole in the bag body.

15. A system for collecting breast milk, the system comprising:
at least one bag comprising a bag body defining a bag interior and a bag opening, the bag body comprising at least one hole at an end margin thereof adjacent the bag opening, a reclosable seal configured to selectively seal the bag spaced apart from the at least one hole relative to the end margin, and a zone of weakness spaced apart between the end margin and the reclosable seal and defining a header portion of the bag; and
an adaptor for securing the bag to a breast pump, the adaptor comprising a wall having an inlet end portion and a spaced apart outlet end portion, the wall defining a flow passage extending along an axis through the inlet end portion and outlet end portion, the inlet end portion being configured to attach to an outlet of a breast pump so that liquid dispensed from the outlet of the breast pump passes through the liquid flow passage and is dispensed from the outlet end portion of the adaptor, the adaptor further comprising a retainer configured to extend through the at least one hole in the bag body to secure the bag to the breast pump to receive the liquid dispensed from the outlet end portion of the adaptor, the adaptor and the bag being sized and arranged so that, when the retainer secures the bag to the adaptor, the reclosable seal can be selectively sealed and the bag body can be subsequently torn along the zone of weakness to separate a sealed portion of the bag from the header portion without removing the header portion from the adaptor;
wherein the adaptor further comprises at least one slot extending through the wall, the at least one slot at least partially defining the retainer, the slot comprising a pair of leg portions and a top connecting portion and the wall tapers toward the inlet end portion of the adaptor so that the top connecting portion of the slot extends laterally inward of at least a portion of the retainer.

16. The adaptor in claim 1 wherein the retainer has a free end and a fixed end, the retainer being joined to the wall at the fixed end, the free end of the retainer being located nearer to the inlet end portion of the wall than to the fixed end of the retainer.

* * * * *